United States Patent
Grady

(10) Patent No.: US 10,991,465 B2
(45) Date of Patent: Apr. 27, 2021

(54) SYSTEMS AND METHODS FOR PERFORMING COMPUTER-SIMULATED EVALUATION OF TREATMENTS ON A TARGET POPULATION

(71) Applicant: HeartFlow, Inc., Redwood City, CA (US)

(72) Inventor: Leo Grady, Millbrae, CA (US)

(73) Assignee: HeartFlow, Inc., Redwood City, CA (US)

(*) Notice: Subject to any disclaimer, the term of this patent is extended or adjusted under 35 U.S.C. 154(b) by 188 days.

(21) Appl. No.: 16/226,204

(22) Filed: Dec. 19, 2018

(65) Prior Publication Data

US 2019/0189286 A1  Jun. 20, 2019

Related U.S. Application Data

(60) Provisional application No. 62/608,483, filed on Dec. 20, 2017.

(51) Int. Cl.
  *G16H 50/50* (2018.01)
  *G16H 10/20* (2018.01)
  *G16H 70/60* (2018.01)

(52) U.S. Cl.
  CPC ............ *G16H 50/50* (2018.01); *G16H 10/20* (2018.01); *G16H 70/60* (2018.01)

(58) Field of Classification Search
  CPC ......... G16H 50/50; G16H 10/20; G16H 70/60
  See application file for complete search history.

(56) References Cited

U.S. PATENT DOCUMENTS

| | | | |
|---|---|---|---|
| 9,339,200 B2* | 5/2016 | Fonte | A61B 5/1073 |
| 2002/0012921 A1* | 1/2002 | Stanton, Jr. | G16H 20/70 |
| | | | 435/6.16 |
| 2003/0211518 A1* | 11/2003 | Slotman | G01N 33/6863 |
| | | | 435/6.16 |
| 2006/0224421 A1 | 10/2006 | St. Ores | |
| 2012/0041739 A1 | 2/2012 | Taylor | |
| 2014/0073977 A1 | 3/2014 | Grady et al. | |
| 2014/0122048 A1 | 5/2014 | Vadakkumpadan | |
| 2014/0249790 A1 | 9/2014 | Spilker et al. | |
| 2014/0249791 A1* | 9/2014 | Taylor | A61B 5/0263 |
| | | | 703/11 |

(Continued)

*Primary Examiner* — Kevin Ky
(74) *Attorney, Agent, or Firm* — Bookoff McAndrews, PLLC

(57) ABSTRACT

Methods and systems may be used for performing computer-simulated evaluation of treatments. For example, the method may include: for each of a plurality of patients, receiving one or more patient-specific anatomical and/or physiological models; selecting, from the plurality of patients, a set of patients that have one or more common characteristics; for each patient in an experimental group, modifying at least one model of the respective one or more patient-specific models to obtain at least one modified patient-specific model that models an effect of an evaluation treatment on the respective patient, and calculating a value of an evaluation endpoint based on the respective at least one modified patient-specific model; and comparing the calculated values of the evaluation endpoint with one or more control values of the evaluation endpoint for patients that satisfy the one or more selection criterion.

20 Claims, 7 Drawing Sheets

(56) References Cited

U.S. PATENT DOCUMENTS

| | | |
|---|---|---|
| 2015/0038860 A1 | 2/2015 | Fonte |
| 2015/0324545 A1* | 11/2015 | Fonte ................. A61B 5/02007 |
| | | 703/2 |
| 2016/0019693 A1* | 1/2016 | Silbersweig ........... G16H 50/20 |
| | | 382/128 |
| 2016/0292382 A1 | 10/2016 | Grady et al. |
| 2016/0306944 A1 | 10/2016 | Grady et al. |
| 2017/0076062 A1 | 3/2017 | Choi et al. |
| 2017/0140109 A1 | 5/2017 | Kheifetz |
| 2018/0182096 A1 | 6/2018 | Grady et al. |

* cited by examiner

SYSTEMS AND METHODS FOR PERFORMING COMPUTER-SIMULATED EVALUATION OF TREATMENTS ON A TARGET POPULATION

RELATED APPLICATION

This application claims priority to U.S. Provisional Application No. 62/608,483, filed on Dec. 20, 2017, the entire disclosure of which is hereby incorporated by reference in its entirety.

TECHNICAL FIELD

Various embodiments of the present disclosure relate generally to systems and methods for performing simulation-based evaluation of treatments, such as medical treatments.

BACKGROUND

Clinical trials may be used to assess the performance of new medical and healthcare treatments, such as new medications, devices, and procedures, in order to establish their safety and efficacy prior to potential commercialization and clinical adoption. However, clinical trials may be expensive and may pose business risks as well as risks to patients, due to the possibility of unexpected negative outcomes.

Given the expense and risks of clinical trials, there is a need for systems and methods to perform digitally simulated trials of treatments in a manner analogous to clinical trials. The results of the digital trials may then be used to assess whether it is worthwhile to pursue clinical trials on live patients or to further invest in the treatment technology. Various embodiments of the present disclosure address one or more of these above-referenced challenges.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, systems and methods are disclosed for performing simulation-based evaluation of treatments.

For example, a method may include: for each of a plurality of patients, receiving one or more patient-specific anatomical and/or physiological models, the one or more patient-specific models including a model of at least a portion of a vasculature of the respective patient; selecting, from the plurality of patients, a set of patients that have one or more common characteristics; identifying an experimental group of patients from the set of patients; for each patient in the experimental group, modifying at least one model of the respective one or more patient-specific models to obtain at least one modified patient-specific model that models an effect of an evaluation treatment on the respective patient, and calculating a value of an evaluation endpoint based on the respective at least one modified patient-specific model, the evaluation endpoint being indicative of a health or medical characteristic of a patient; and comparing the calculated values of the evaluation endpoint with one or more control values of the evaluation endpoint for patients that satisfy the one or more selection criterion.

For example, a computer system may include a memory storing instructions and one or more processors configured to execute the instructions to perform operations. The operations may include: for each of a plurality of patients, receiving one or more patient-specific anatomical and/or physiological models, the one or more patient-specific models including a model of at least a portion of a vasculature of the respective patient; selecting, from the plurality of patients, a set of patients that have one or more common characteristics; identifying an experimental group of patients from the set of patients; for each patient in the experimental group, modifying at least one model of the respective one or more patient-specific models to obtain at least one modified patient-specific model that models an effect of an evaluation treatment on the respective patient, and calculating a value of an evaluation endpoint based on the respective at least one modified patient-specific model, the evaluation endpoint being indicative of a health or medical characteristic of a patient; and comparing the calculated values of the evaluation endpoint with one or more control values of the evaluation endpoint for patients that satisfy the one or more selection criterion.

Furthermore, a non-transitory computer-readable medium storing instructions that, when executed by one or more processors of a computer system, cause the one or more processors to perform a method for performing computer-simulated trials of treatments. The method may include: for each of a plurality of patients, receiving one or more patient-specific anatomical and/or physiological models, the one or more patient-specific models including a model of at least a portion of a vasculature of the respective patient; selecting, from the plurality of patients, a set of patients that have one or more common characteristics; identifying an experimental group of patients from the set of patients; for each patient in the experimental group, modifying at least one model of the respective one or more patient-specific models to obtain at least one modified patient-specific model that models an effect of an evaluation treatment on the respective patient, and calculating a value of an evaluation endpoint based on the respective at least one modified patient-specific model, the evaluation endpoint being indicative of a health or medical characteristic of a patient; and comparing the calculated values of the evaluation endpoint with one or more control values of the evaluation endpoint for patients that satisfy the one or more selection criterion.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
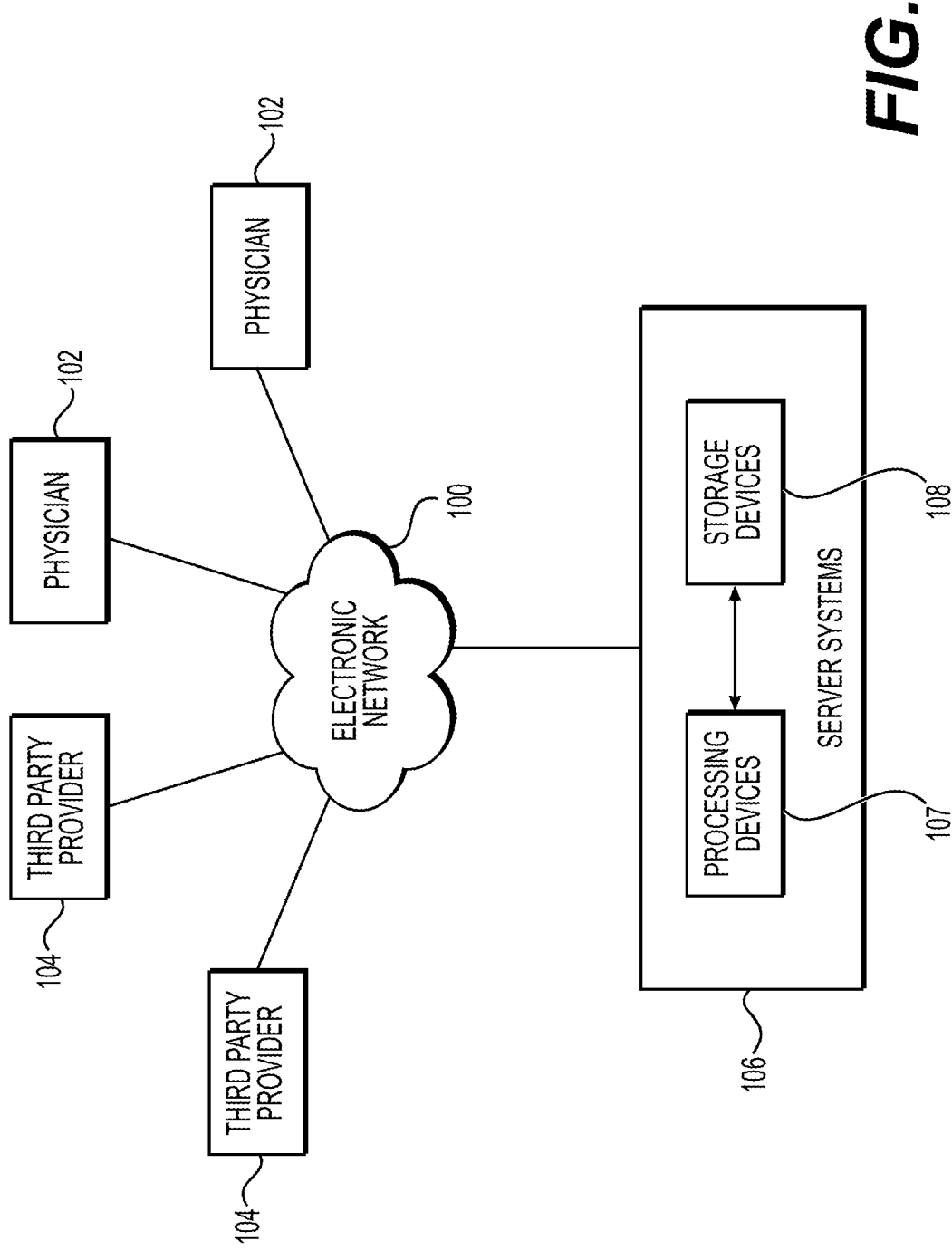
FIG. 1 depicts an example of an environment in which a computer system for performing computer-simulated evaluation of treatments may be implemented, according to one or more embodiments.

The present disclosure generally relates to simulation-based evaluation (e.g., computer-simulated experimentation) of medical treatments and other forms of treatments. In general, the effect or administration of a treatment on a patient may be modeled using patient-specific anatomical or physiological models generated from medical images of that patient. By modeling the treatment, an evaluation endpoint indicative of the outcome of the treatment may then be calculated using the model. The calculated evaluation endpoint therefore provides a simulated outcome of the treatment for a particular patient. By performing such simulations across a number of patients, it becomes possible to obtain simulated outcomes for a population. This population may, for example, be patients with a particular disease or medical condition.

The evaluation may be a controlled, simulated experiment using patient-specific models generated from medical images of a plurality of patients. As will be discussed in more detail below, patients may be assigned to experimental and control groups. By using patient-specific models for patients in both the experimental group and the control group, it is possible to model the effect or application of the treatment in just the experimental group, and not the control group. Accordingly, it is possible to compare values of the evaluation endpoint for the experimental group with values of the evaluation endpoint for the control group.

In some examples, the simulation-based evaluation may evaluate a treatment, such as a drug or medical device, that is typically subject to clinical trials. In such examples, the evaluation may be referred to as a simulated clinical trial or digital clinical trial. However, simulation-based evaluations according to this disclosure may broadly encompass the evaluation of any health-affecting factor capable of evaluation using the methods described in this disclosure. That is, the treatments that may be evaluated by the methods described in this disclosure are not limited to treatments that are typically subject to clinical trials, but may encompass health-affecting factor such as medical policy. Therefore, evaluations according to this disclosure may be, for example, a population study or epidemiology study. The terms "evaluation" and "assessment" may be used interchangeably.

In the following description, embodiments will be described with reference to the accompanying drawings. The terminology used in this disclosure may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a" and "an" include plural referents unless the context dictates otherwise. The term "exemplary" is used in the sense of "example" rather than "ideal." The term "one or more of," when followed by a list of items defined using the conjunction "and," is an alternative expression that means either one of the listed items or more than one of the listed items. The terms "comprises," "comprising," "includes," "including," and other variations thereof, are intended to cover a non-exclusive inclusion such that a process, method, or product that comprises a list of elements does not necessarily include only those elements, but may include other elements not expressly listed or inherent to such a process, method, article, or apparatus.

In this disclosure, the term "subset" generally does not require a "strict subset" (a subset that is strictly smaller than the base set from which the subset is selected). In general, a subset of a base set may be equal to or smaller than the base set. However, whenever a subset is described for a certain aspect of the disclosure, it is understood that a strict subset is also specifically disclosed for that aspect.

FIG. 1 depicts an environment in which a computer system for performing digital trials of treatments may be implemented. The environment includes server systems 106, which constitute an example of such a computer system. The environment further includes a plurality of physicians 102 and third party providers 104, any of which may be connected to an electronic network 100, such as the Internet, through one or more computers, servers, and/or handheld mobile devices. In FIG. 1, physicians 102 and third party providers 104 may each represent a computer system, as well as an organization that uses such a system. For example, a physician 102 may be a hospital or a computer system of a hospital.

Physicians 102 and/or third party providers 104 may create or otherwise obtain medical images, such as images of the cardiac, vascular, and/or organ systems, of one or more patients. Physicians 102 and/or third party providers 104 may also obtain any combination of patient-specific information, such as age, medical history, blood pressure, blood viscosity, and other types of patient-specific information described below. Physicians 102 and/or third party providers 104 may transmit the cardiac/vascular/organ images and/or patient-specific information to server systems 106 over the electronic network 100.

Server systems 106 may include one or more storage devices 108 for storing images and data received from physicians 102 and/or third party providers 104. The storage devices 108 may be considered to be components of the memory of the server systems 106. Server systems 106 may also include one or more processing devices 107 for processing images and data stored in the storage devices and for performing any computer-implementable process described in this disclosure. Each of the processing devices 107 may be a processor or a device that include at least one processor. In some embodiments, server systems 106 may have a cloud computing platform with scalable resources for computations and/or data storage, and may run an application for performing processes described in this disclosure on the cloud computing platform.

Other examples of computer systems for performing digital evaluation of treatments include desktop computers, laptop computers, and mobile computing devices such as tablets and smartphones. In general, a computer system may be a single device or a plurality of devices. A computer system may include a memory storing instructions and one or more processors configured to execute the instructions to perform various operations. The memory may include any combination of volatile memory and non-volatile memory, and may store data, such as patient-specific models and patient-specific information, in addition to the instructions.

Figure 2:
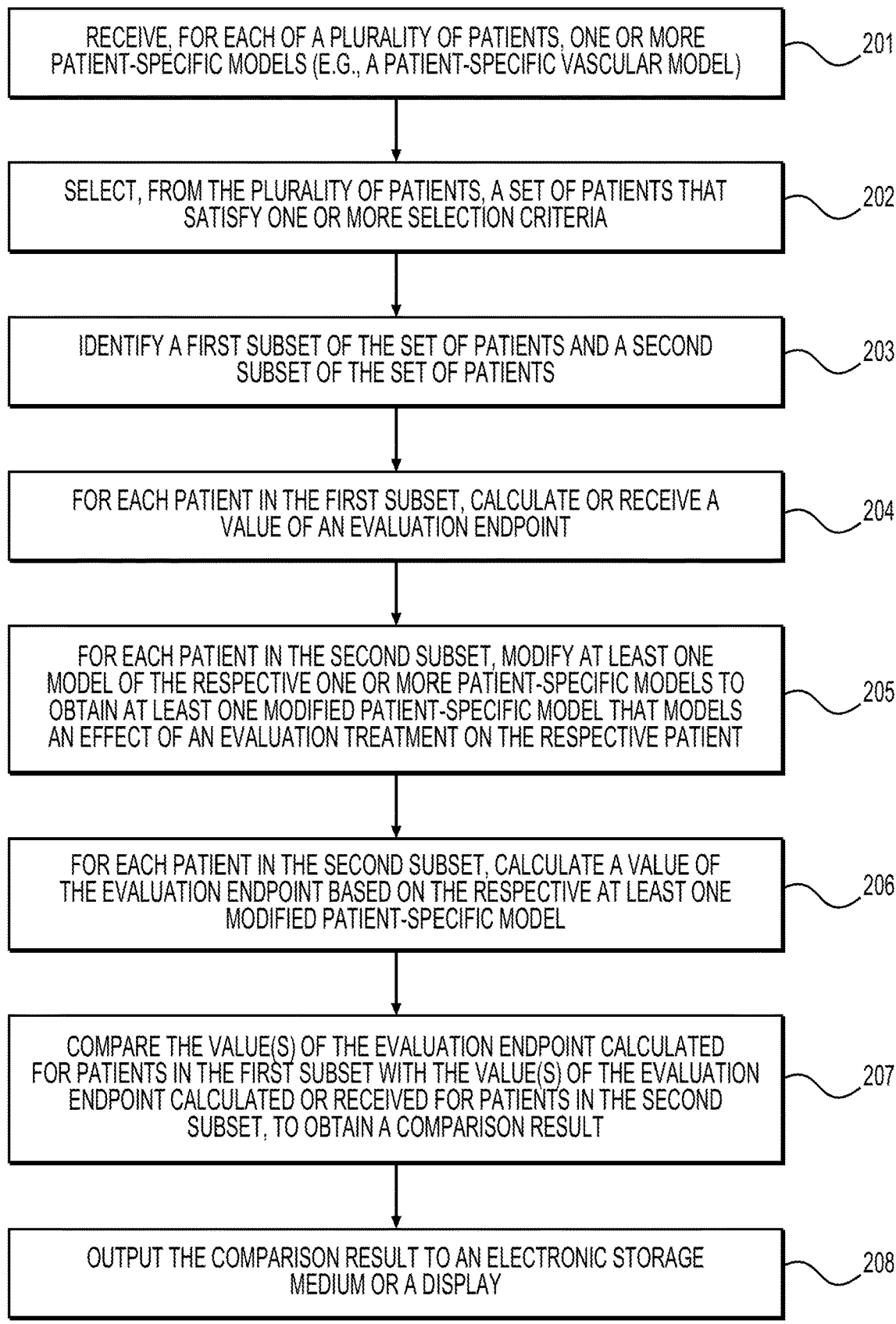
FIG. 2 depicts a flowchart of a method of performing computer-simulated trials of treatments, according to one or more embodiments.

FIG. 2 illustrates a method for simulation-based evaluation of treatments. Any or all of the steps in FIG. 2, as well as various other computer-implementable processes discussed below, may be performed by one or more processors of a computer system, such as sever systems 106 or a computer system of any suitable type.

Step 201 may include receiving, for each of a plurality of patients, one or more patient-specific models. The one or more patient-specific models may each be an anatomical and/or physiological model, which denotes a model that is either anatomical, physiological, or both anatomical and physiological. The process of receiving a patient-specific model may include generating the model at the computer system or receiving the model over the electronic network, such as electronic network 100. Any model that is generated at the computer system or received by the computer system over the network may be stored in a memory component of the computer system, such as storage devices 108.

The one or more patient-specific models received for each of the plurality of patients may include one or more patient-specific models of at least a portion of a vasculature of the respective patient. Such models may be referred to as vascular models or vessel models, and models may be anatomical and/or physiological models. Examples of types of vasculature that may be represented by a patient-specific vascular model include, but are not limited to, coronary vasculature, peripheral vasculature, cerebral vasculature, renal vasculature, visceral vasculature, and hepatic vasculature such as portal veins. A patient-specific vascular model may represent one or more than one of the above types of vasculature, and may indicate disease progression or regression, plaque rupture, thrombosis, and other characteristic of the represented vasculature(s). A patient-specific vascular model may be a single vascular model or a plurality of vascular models. In some embodiments, a patient-specific vascular model may comprise one or more three-dimensional models and one or more reduced-order (e.g., one-dimensional) models. The term "vascular model" or "vessel model" does not limit the model to representing only vasculature.

In some embodiments, the patient-specific models received across all patients includes a plurality of patient-specific vascular models respectively received for the plurality of patients. In such embodiments, the plurality of patient-specific vascular models may represent the same type of vasculature across different patients, and each particular one of the plurality of patient-specific vascular models may additionally represent characteristics of the vasculature that are specific to the respective patient.

The one or more patient-specific models received for each of the plurality of patients may additionally or alternatively include one or more patient-specific models representing at least a portion of a tissue of the respective patient. Such models may be referred to as tissue models, and may be anatomical models. Examples of types of tissues that may be represented by a tissue model include, but are not limited to, myocardial heart tissue, muscles in the peripheral aspects of the body, brain tissue, kidney tissue, and tissue of other internal organs such as the liver, stomach, spleen, intestines, colon, lungs, and pancreas. A patient-specific tissue model may represent one or more than one of the above types of tissues, and may represent vessels in addition to tissues. A patient-specific tissue model may be a single tissue model or a plurality of tissue models. In some embodiments, a patient-specific tissue model may comprise one or more three-dimensional models and one or more reduced-order (e.g., one-dimensional) models.

In some embodiments, the entire set of patient-specific models received across all patients includes a plurality of patient-specific tissue models respectively received for the plurality of patients. In such embodiments, the plurality of patient-specific tissue models may all represent the same type of tissue across different patients, and each particular one of the plurality of patient-specific tissue models may further represent characteristics of the vasculature that are specific to the respective patient.

In some embodiments, the one or more patient-specific models received for each of the plurality of patients includes both one or more patient-specific vascular models and one or more patient-specific tissue model. In such embodiments, the one or more patient-specific tissue models may include a representation of a tissue whose blood perfusion is dependent on a vasculature that is represented by the one or more patient-specific vascular model. For example, the vasculature may transport blood to or from the tissue.

Any anatomical and/or physiological model described above may be generated from one or more images of the patient acquired using an imaging or scanning modality. Examples of imaging or scanning modalities include computed tomography (CT) scans, magnetic resonance (MR) imaging, micro-computed tomography (μCT) scans, micro-magnetic resonance (μMR) imaging, dual energy computed tomography scans, ultrasound imaging, single photon emission computed tomography (SPECT) scans, and positron emission tomography (PET) scans. In embodiments in which the model is generated at the computer system, the computer system (e.g., server systems 106) may first receive such images of the patient from a certain source, such as physicians 102 and/or third party providers 104, and then generate a model based on the received images.

Each of the plurality of patients may be associated with patient-specific information. In some embodiments, patient-information information may be received over a network from a source, such as physicians 102 and/or third party providers 104. The receipt of the patient-specific information may occur prior to step 202. In some embodiments, step 201 may include receiving patient-specific data in general, wherein the patient-specific data includes both the aforementioned one or more patient-specific models and the patient-specific information.

Patient-specific information may include any one or combination of the following: patient profile information, patient medical information, patient behavioral information, patient lifestyle information, patient environment information, product usage information, annotations or comments for patient-specific models, and other information describing a specific patient. It is noted that these categories may overlap.

Examples of patient profile information include demographic information of the patient (e.g., gender, age, ethnicity), the geographical location of the patient, and the genetic profile of the patient. Examples of medical information include information indicating the patient's disorders, illnesses and comorbidities (e.g., diabetes, hypertension, etc.); information indicating previous procedures of the patient (e.g., stent, angioplasty, surgery, bypass, valve replacement, amputation, organ transplant, etc.); pathological information of the patient (e.g., plaque type, a percentage of stenosis, vessel size, diffuse intimal thickening, infarct, viability, ischemia, vascular steal, total occlusion, plaque vulnerability, aneurysm, tumor, lesion, perfusion defect, etc.); medical and physiological measurements of the patient (e.g., FFR, CFR, iFR, SYNTAX, etc.); other anatomical characteristics (e.g., the presence of a particular vessel course, such as a ramus branch, the presence of extensive branching pattern, etc.); and other physiological characteristics. Medical information may include a medical history of the patient. Examples of patient environment information include information indicating environmental factors (e.g., local air quality, local water quality, etc.) to which the patient is subjected to.

In some embodiments, the patient-specific information and the one or more patient-specific models may be compiled into a database that is stored in a memory component of the computer system, such as storage devices 108. The database may associate each of the patient-specific model and each patient-specific information with a patient identifier corresponding to a particular patient, such that for any given patient identifier corresponding to a particular, all patient-specific models that represent a vasculature or tissue of that particular patient may be identified and retrieved from the database.

Step 202 may include selecting, from the plurality of patients, a set of patients that satisfy one or more selection criteria. The one or more selection criteria may depend on the particular application of the method of FIG. 2, and may be input into the computer system (e.g., as a user input). When the method of FIG. 2 is used to conduct digital clinical trials on a certain target population or evaluation of potential treatments for a certain target population, the selected set of patients may be representative of that target population. For example, the selection criteria may be a characteristic shared by the target population. Additionally, in order to represent a target population, the number of patients in the set may be of a sufficiently large number.

In various embodiments, the one or more selection criteria may be a patient having one or more specified characteristics expressly indicated by, or discernable by analysis of, the patient-specific information and/or one or more patient-specific models. Such characteristics may include a demographical characteristic, a medical or health-related characteristic, a behavioral characteristic, a lifestyle characteristic, and/or a patient environment characteristic. Examples of medical or health-related characteristics include anatomical characteristics, physiological characteristics, genetic characteristics, pathological characteristics, comorbidies, and characteristics indicated by clinical parameters. For example, in step 202, the set of patients may be selected on the basis that each patient in the set satisfies one or more of the following criteria: having a certain gender, age (or age range), and/or ethnicity; having one or more co-morbidities (e.g., diabetes, hypertension, etc.); having undergone a one or more treatment procedures (e.g., stent, angioplasty, surgery, bypass, valve replacement, amputation, organ transplant, etc.); having a certain pathology (e.g., plaque type, a percentage of stenosis, vessel size, diffuse intimal thickening, infarct, viability, ischemia, vascular steal, total occlusion, plaque vulnerability, aneurysm, tumor, lesion, perfusion defect, etc.); being located in a certain geographical area; having a certain genetic profile, patient behavior, diet, and/or lifestyle; having been subject to certain environmental factors (e.g., local air quality, local water quality, etc.); having used a certain product; having a measured score (e.g., FFR, CFR, iFR, SYNTAX, etc.) of a certain value or range of values; and/or having certain anatomical features (e.g., presence of a particular vessel course, such as a ramus branch, extensive branching pattern, etc.).

The method of FIG. 2 may be used to evaluate a treatment on the basis of an evaluation endpoint. A treatment to be evaluated may be referred to as an "evaluation treatment." An evaluation treatment may encompass any medical or health-impacting treatment for a patient or an event (such as an environmental change) with potential health-related effects on a patient. Examples of evaluation treatments include, but are not limited to, revascularization, surgery, medications, weight gain or loss, organ transplants, recanalization, social policy changes (e.g., medical care policy changes), diet changes, smoking cessation, relocation, environmental changes (e.g., urban development and land use projects), genetic changes, plaque regression or progression, immunotherapy, and use of a medical device or implant. In this disclosure, "treatment" is not limited to remedial treatments.

An evaluation endpoint may be a variable or parameter whose value is computable using any one or more of the patient-specific model(s) respectively associated with a patient. Such variable or parameter may be indicative of one or more medical or health characteristics of a patient. Examples of evaluation endpoints include, but are not limited to: fractional flow reserve (FFR); instantaneous wave-free ratio (iFR); coronary flow reserve (CFR); synergy between PCI with *Taxus* and Cardiac Surgery (SYNTAX) score; Major Adverse Cardiac Events (MACE) or a risk of MACE; percent stenosis; an indicia, value, or characteristic of perfusion; an indicia, value, or characteristic of plaque regression and/or progression; an indicia, value, or characteristic of plaque rupture; an indicia, value, or characteristic of thrombosis; and an indicia, value, or characteristic of organ function. The value of an evaluation endpoint may be calculated by computations based on the characteristics of the patient-specific model(s) or simulations performed using the model(s). In some embodiments, the evaluation endpoint may pertain to a particular aspect of a model, such as the FFR of a particular artery represented in a vascular model.

In some embodiments, the computer system or a user of the computer system may receive the evaluation treatment and the evaluation endpoint. The evaluation treatment may be received by the computer system or the user of the computer system in the form of a description of the evaluation treatment, a description of modeling parameters used to model the effect of the evaluation treatment using a patient-specific model, or a description of an expected result (of the evaluation treatment) that can be modeled in the one or more patient-specific models. The modeling parameters and the evaluation endpoints, if not received by the computer system, may be input into the computer system by a user, so that the computer system may perform the modeling and calculations in steps 205 and 206, discussed below, based on the input.

Step 203 may include identifying a first subset of the set of patients and a second subsets of the set of patients. In some embodiments, the second subset may be used as an experimental group that is to be subjected to a digitally modeled application of the evaluation treatment, and the first subset may be used as a control group. In general, the first and second subsets may each be less than or equal to the set of patients selected in step 202.

The first and second subsets may be overlapping in that a patient may belong to both of the first and second subsets. In some examples, the first subset and the second subset may be the same as one another, and both may furthermore be the same as the set of patients selected in step 202. Alternatively, the first and second subsets may be non-overlapping. Selection of the first and second subsets may be based on any suitable methodology, such as random selection of patients to one of the subsets followed by assignment of the remainder of patients of to the other subset.

Step 204 may include, for each patient in the first subset (e.g., control group), calculating or receiving a value of the evaluation endpoint. This step may be performed by calculating a respective value for each patient in the first subset based on the one or more patient-specific models. This calculation may utilize the one or more patient-specific models in a manner analogous to the corresponding calculation for the second subset in step 206 discussed below.

Step 205 may include, for each patient in the second subset (e.g., experimental group), modifying at least one model of the respective one or more patient-specific models to obtain at least one modified patient-specific model that models an effect of an evaluation treatment on the respective patient. For example, if the one or more patient-specific models associated with a particular patient includes a vascular model and a tissue model, then either one or both of these models may be modified in a way that models an effect resulting from the use or administration of the evaluation treatment on that particular patient. This process may be repeated for each patient in the second subset.

The process of modifying a model to represent the evaluation treatment may also be referred to as a process of digital applying the evaluation treatment to the patient corresponding to the model. The modification may be in accordance with the aforementioned modeling parameters of the evaluation treatment. That is, the modeling parameters of the evaluation treatment may specify how the at least one model is to be modified to represent application of the evaluation treatment. Such modification may include adjustment of one or more parameters of the patient-specific models. For example, the modification to an anatomical model may modify a parameter describing the geometry of the vasculature or tissue.

For example, if the evaluation treatment is expected to increase blood flow cross-sectional area of a part of a blood vessel available for blood flow, and the part of a blood vessel is modeled by an anatomical vascular model, then the modification may include adjusting a parameter of the anatomical vascular model that represents the cross-sectional area available for blood flow. If there is a plurality of patient-specific models, then the plurality of patient-specific models may be said to be modified if any one of the plurality of models is modified.

Step 206 may include, for each patient in the second subset, calculating a value of the evaluation endpoint based on the respective at least one modified patient-specific model. The calculated value of the evaluation endpoint may therefore be referred to as a simulated result of the treatment on the respective patient. Examples of methods for using models to model various treatments and performing subsequent computations are described in, for example, US 2012/0041739 A1 to Taylor and US 2014/0249790 to Spilker et al., each of which is hereby incorporated by reference in its entirety.

In embodiments in which the one or more patient-specific models is a plurality of patient-specific models for each patient, then the result of the calculation may be dependent on all of the plurality of patient-specific models for that patient, even if not all of the models were modified in step 204. For example, if the one or more patient-specific models include both a vascular model and a tissue model (e.g., of a tissue supplied by a vessel represented by the vascular model) and only the former is modified in step 206, then the evaluation endpoint for the patient may still be dependent, directly or indirectly, on the unmodified tissue model. In some examples, the tissue model may be used to define parameters of or associated with the modified vascular model. For example, in the case of calculating FFR, a tissue model of myocardial tissue may be used to determine certain parameters, such as myocardial mass. Such parameters may be used to determine values for boundary conditions when calculating FFR.

As another example, modification of the vascular model may affect the simulation of tissue model characteristics such as blood perfusion through the tissue model. Further examples of methods for performing computations based on vascular and tissue models are described in, for example, US 2016/0306944 A1 to Grady et al., US 2017/0076062 A1 to Choi et al., and US 2016/0292382 to Grady et al., each of which is hereby incorporated by reference in its entirety.

In some examples, the calculation of the evaluation endpoint may utilize one or more machine learning models trained to calculate the endpoint based on a given set of inputs, which may include anatomical and/or physiological characteristics indicated by or derived from any of the one or more patient-specific models. Examples of methods that utilize machine learning models are described in, for example, US 2014/0073977 A1 to Grady et al., and US 2018/0182096 A1 to Grady et al. each of which is hereby incorporated by reference in its entirety.

While step 204 is listed before steps 205-206 in FIG. 2, step 204 may be performed either prior to, concurrently with, or subsequent to steps 205-206. If step 204 occurs after steps 205-206, then the models used in step 204 may be the one or more patient-specific models without the modifications of step 205. In general, when a modified model is generated in step 205, the original model used to generate the modified may be retained for any subsequent use.

Step 207 may include comparing the value(s) of the evaluation endpoint calculated for patients in the first subset with the value(s) of the evaluation endpoint calculated or received for patients in the second subset, to obtain a comparison result. If the first subset is the control group, the values of the evaluation endpoint calculated or received in step 204 may also be referred as control values or baseline values. Similarly, if the second subset is the experimental group, the values of the evaluation endpoint calculated in step 206 may also be referred to as experimental values.

The comparison result may indicate an outcome of the virtual clinical trial or other evaluation of the evaluation treatment. Step 207 may compare the two sets of values based on any suitable methodology. Such comparison may be between representative values of the two sets of values. For example, the comparison may be a comparison of the mean of all values of the evaluation endpoint calculated or received in step 204 with the mean of all the values of the evaluation endpoint calculated in step 206. In some embodiments, the method may further include calculating the risk and/or cost assessment of the impact of the treatment on patients in the second subset as compared to patients in the first subset.

Step 208 may include outputting the comparison result to an electronic storage medium or a display. The electronic storage medium may be a memory component of the computer system (such storage devices 108), a cloud storage (internal or external to the computer system), or another processing device (such as an external computer, smartphone or tablet), which may be connected to the computer system by an electronic network. Additionally or alternatively, the values of the evaluation endpoint calculated in steps 204 and 206 may also be output to an electronic storage medium or a display.

As mentioned earlier, clinical trials of drugs, devices, and other treatments on live patients may be expensive and may pose risks. The method of FIG. 2 permits an evaluation, such as a clinical trial, to be performed digitally. The results of the digital trial or other evaluation may be used to improve the design of or to avoid the necessity of actual clinical trials altogether. Accordingly, risks associated with actual clinical trials may be reduced. It is noted that the method of FIG. 2 is not limited to simulations that replicate clinical trials, but extends to evaluation of treatments in general. Additional example implementations of the method are described below.

Figure 3:
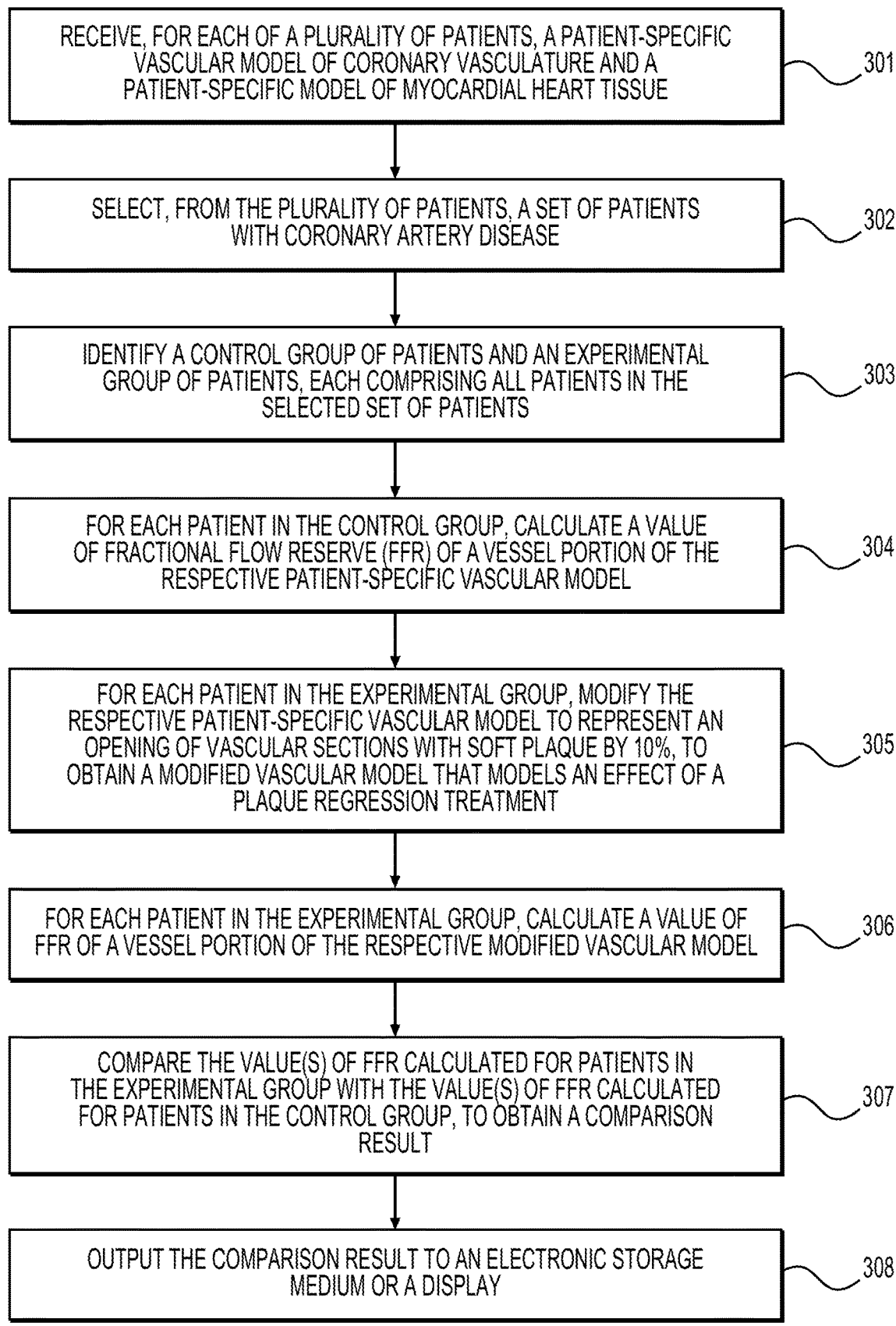
FIG. 3 depicts a flowchart of a method of performing computer-simulated trials for a treatment for plaque regression, according to one or more embodiments.

FIG. 3 illustrates an example of a method for performing digital clinical trials to evaluate new agents or drugs for treating coronary artery disease. For example, a pharmaceutical company may desire to test a new agent (e.g., medication) that it believes may be able to regress soft plaque by a certain amount (10%, for example) when administered as a plaque regression treatment. Before testing the new agent in live human subjects, the pharmaceutical company may desire to know the impact of the agent on the population of patients with coronary artery disease (as evaluated by fractional flow reserve (FFR), for example), if the company were to go forward with the development of the new agent.

The method illustrated by FIG. 3 may include steps 301-308, as will be discussed below. These steps may be understood as examples of steps 201-208 of the method illustrated by FIG. 2, respectively.

Step 301 may include receiving, for each of a plurality of patients, a patient-specific vascular model of coronary vasculature and a patient-specific model of myocardial heart tissue. The patient-specific vascular model may be a physiological and/or anatomical model. The patient-specific model of myocardial heart tissue may be an anatomical model. The models, along with patient-specific information for each of the plurality of patients, may be compiled in a database.

Step 302 may include selecting, from the plurality of patients, a set of patients with coronary artery disease. The characteristic of having coronary artery disease may be expressly indicated by, or otherwise discernable from, the patient-specific information and/or patient-specific models (e.g., indicated by annotations made by a physician). In some embodiments, the selection criterion may particularly be patients having a certain characteristic of coronary artery disease, such as patients having more than 50% stenosis.

Step 303 may include identifying an experimental group of patients and a control group of patients. In the instant example, both the experimental group and the control group comprise all patients in the selected set of patients. That is, set of patients selected in step 302 is reused for both the control group and the experimental group.

Step 304 may include, for each patient in the control group, calculating a value of fractional flow reserve (FFR) of a vessel portion of the respective patient-specific vascular model. The calculated FFR may depend on the respective patient-specific tissue model. For example, boundary conditions when calculating FFR may be based on parameters, such as myocardial mass, extracted from the patient-specific model of myocardial heart tissue, which may be a three-dimensional model. In some examples, the patient-specific tissue model is optional. For example, the myocardial mass or such parameters may be known from other sources.

Step 305 may include, for each patient in the experimental group, modifying the respective patient-specific vascular model to represent an opening of vascular sections with soft plaque by 10%, to obtain a modified vascular model that models an effect of the plaque regression treatment. Prior to step 305, the party or computer system performing the method may receive a description of the agent to regress soft plaque. The agent may be what is intended to be tested in the digital clinical trial. The description may include, for example, one or more of a dosage, a concentration, chemical properties, a mode of intake, time and frequency of intake, location of intake, etc. The description may indicate that the agent, when administered in a plaque regression treatment, is expected to reduce plaque by 10%. Thus, in step 304, the opening of vascular sections with soft plaque by 10% may represent the effect of the treatment. In the example of FIG. 3, the evaluation endpoint may be FFR.

Step 306 may include, for each patient in the experimental group, calculating a fractional flow reserve (FFR) value of a vessel portion of the respective modified vascular model. As in step 304, the calculated FFR depend on the respective patient-specific tissue mobile. In steps 304 and 306, the vessel portion for FFR calculation may be a model representation of a diseased or stenosis vessel segment. For the same respective patient, the vessel portion in step 304 and the vessel portion in step 306 may both represent the same vessel segment of that patient.

Step 307 may include comparing the value(s) of FFR calculated for patients in the experimental group with the value(s) of FFR calculated for patients in the control group, to obtain a comparison result. The comparison result may be output to an electronic storage medium or a display (step 308).

The calculated FFR values or the comparison result step 307 may be used by the pharmaceutical company to better assess the likely impact to the target treatment population for the proposed agent before making further investments.

Figure 4:
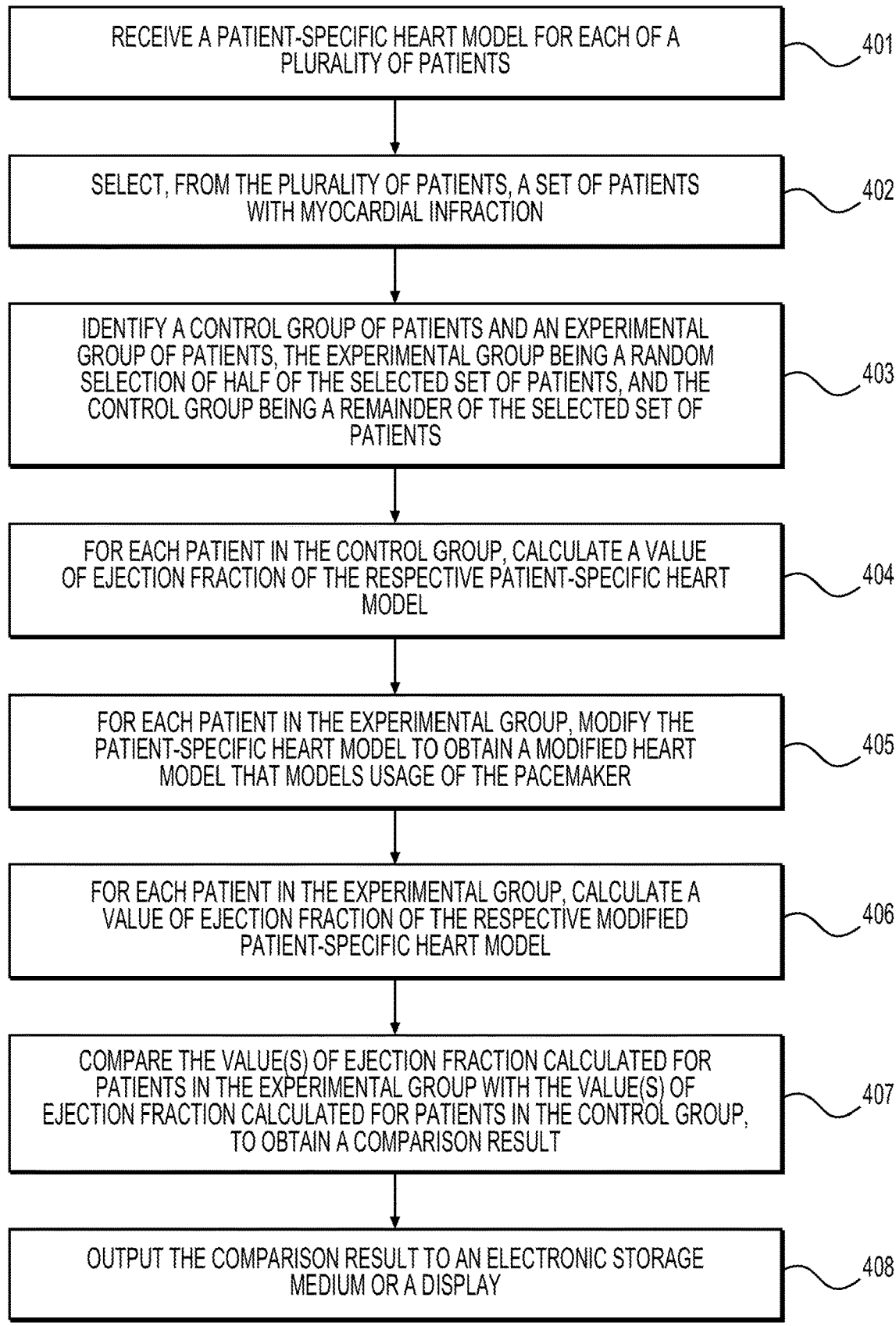
FIG. 4 depicts a flowchart of a method of performing computer-simulated trials for the use of a medical device, according to one or more embodiments.

FIG. 4 illustrates an example of a method for performing digital clinical trials to evaluate a new medical device or implant, such as a new pacemaker. As an example of a scenario in which the method may be utilized, a biomedical company may desire to test a new pacemaker design that is expected to increase a patient's ejection fraction. Before testing the new pacemaker in live human subjects, the biomedical company may evaluate the impact on the ejection fraction in population of patients with a myocardial infarction.

The method illustrated by FIG. 4 may include steps 401-408, as will be discussed below. These steps may be understood as examples of steps 201-208 of the method illustrated by FIG. 2, respectively.

Step 401 may include receiving a patient-specific heart model for each of a plurality of patients. The heart model may model anatomical and/or physiological aspects of the patient's heart. The heart models, along with patient-specific information for each of the plurality of patients, may be compiled in a database.

Step 402, which is an example of step 202, may include selecting, from the plurality of patients, a set of patients with a myocardial infarction. Patients who have a myocardial infarction may be indicated by or discernable from the patient-specific information compiled in the database.

Step 403 may include identifying an experimental group of patients and a control group of patients. In the instant example, the experimental group is a random selection of half of the set of patients with a myocardial infarction, and the control group is a remainder of the set of patients with a myocardial infarction.

Step 404 may include for each patient in the control group, calculating a value of ejection fraction of the respective patient-specific heart model.

Step 405 may include, for each patient in the experimental group, modifying the patient-specific heart model to obtain a modified heart model that models usage of the pacemaker. The modified heart model may, for example, be obtained by digitally stimulating the heart model with an electric map provided by the pacemaker's design. That is, the modified heart model may include a representation of such stimulation. Prior to step 405, the party or computer system performing the method may receive a description of the new pacemaker device and/or its activation, and may further receive an ejection fraction as the evaluation endpoint. The pacemaker device and/or its activation may be what is intended to be tested in the digital clinical trial or evaluation. The description may include, for example, the pacemaker's design, an electrical map based on the pacemaker design, short term and long term effects, activation properties, locations and methods of insertion, geometric properties, physiological properties and effects, electrical and mechanical properties, etc. In the instant example, the electric map may serve as the modeling parameter for step 404.

Step 406 may include, for each patient in the experimental group, calculating a value of ejection fraction of the respective modified patient-specific heart model.

Step 407 may include comparing the value(s) of ejection fraction calculated for patients in the experimental group with the value(s) of ejection fraction calculated for patients in the control group, to obtain a comparison result. The method shown in FIG. 4 may further include outputting the comparison result to an electronic storage medium or a display (step 408).

The calculated values of ejection fraction or the comparison result may be used by the biomedical company to assess the likely impact to the target treatment population for the proposed pacemaker design before making further investments.

Figure 5:
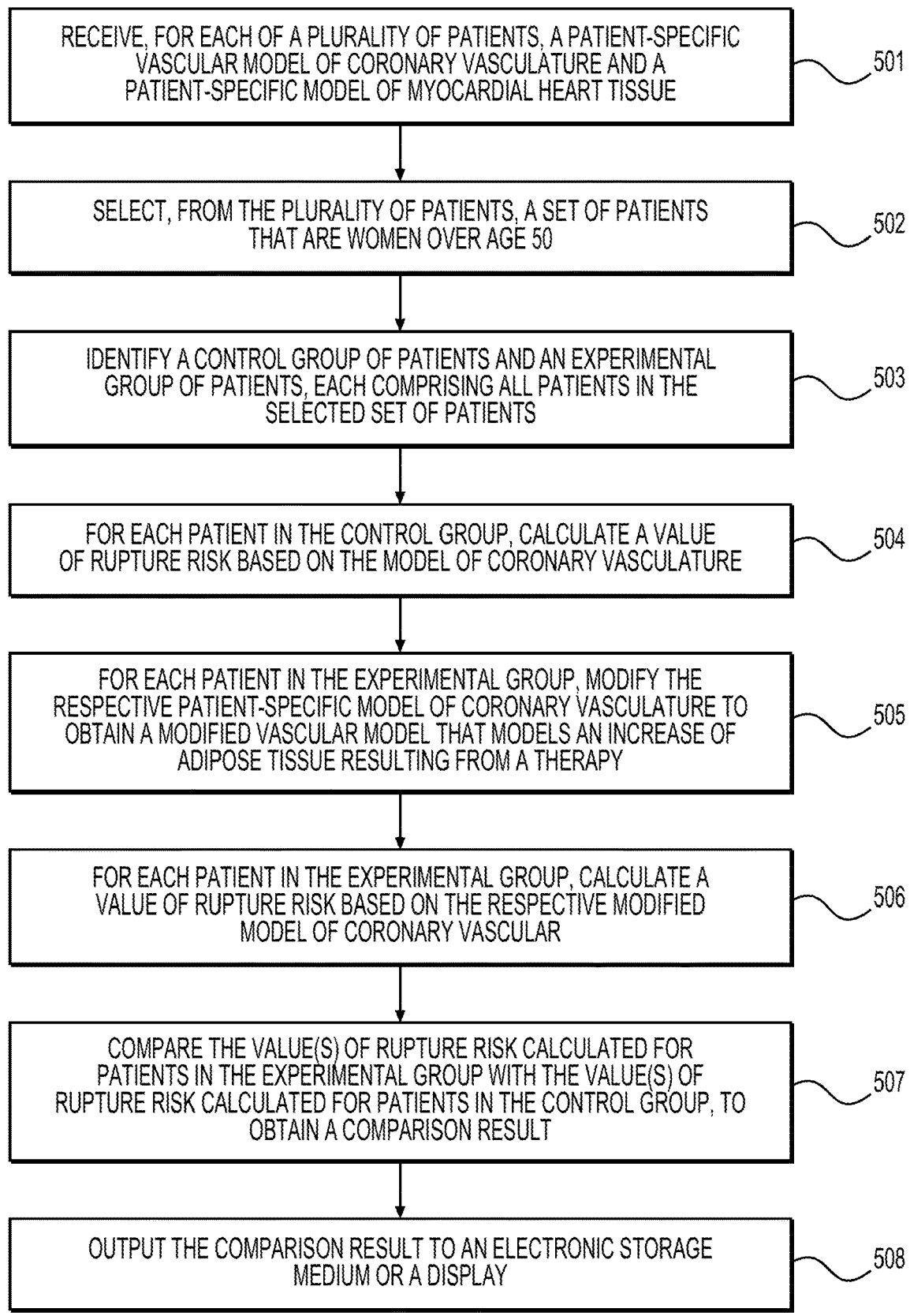
FIG. 5 depicts a flowchart of a method of performing computer-simulated trials of a therapy treatment, according to one or more embodiments.

FIG. 5 illustrates an example of a method for performing digital clinical trials for a new cancer therapy. As an example of a scenario in which the method may be utilized, a pharmaceutical company may desire to test a new chemotherapy for post-menopausal women with ovarian cancer. For example, initial studies conducted by the company may have demonstrated significant weight gain in women who have had the therapy. Therefore, the pharmaceutical company may desire to assess the increased likelihood of major adverse cardiac events (MACE) if they were to market this new therapy to a larger population.

The method illustrated by FIG. 5 may include steps 501-508, as will be discussed below. These steps may be understood as examples of steps 201-208 of the method illustrated by FIG. 2, respectively.

The method illustrated by FIG. 5 may include: receiving, for each of a plurality of patients, a patient-specific vascular model of coronary vasculature and a patient-specific model of myocardial heart tissue (step 501); selecting, from the plurality of patients, a set of patients that are women over age 50 (step 502); and identifying a control group of patients and an experimental group of patients, each comprising all patients in the set of patients that are women over age 50 (step 503). Steps 501-503 may be performed in a manner analogous to that of steps 301-303 of FIG. 3, but with a different selection criteria. This selection of patients that are women over age 50 may be based on the patient profiles compiled in the database.

Step 504 may include, for each patient in the experimental group, calculate a value of rupture risk based on the model of coronary vasculature. In some embodiments, the calculated value may depend on the patient-specific model of myocardial heart tissue.

Step 505, may include, for each patient in the experimental group, modifying the respective patient-specific model of coronary vasculature to obtain a modified vascular model that models an increase of adipose tissue resulting from the therapy that is to be evaluated. An increase of adipose tissue may be model by an increase in the microvascular resistance. Microvascular resistance may be represented by various parameters of the patient-specific model of coronary vasculature.

Prior to step 505, the party or computer system performing the method may receive a description of the therapy, and may further receive an evaluation endpoint. The description of the therapy may include, for example, details on its administration, and short and long term effects. For example, an effect of the therapy may include an increase in weight gain. In order to simulate this effect of the therapy for purpose of the method of FIG. 5, an increase of adipose tissue may be represented by an increase in patient microvasculature resistance. The evaluation endpoint may be MACE or a measurement or assessment of MACE. For example, plaque rupture may be used as the measurement or assessment of MACE.

Step 506 may include, rupture risk based on the model of coronary vasculature (without the modification to model the increase of adipose tissue). In some embodiments, the calculated value may depend on the patient-specific model of myocardial heart tissue.

Step 507 may include comparing the calculated values of rupture risk for patients in the experimental group and the calculated values of rupture risk for patients in the control group. The method may further include outputting the comparison result to an electronic storage medium or a display (step 508).

The calculated values of rupture risk or the comparison results may be used by the pharmaceutical company to assess the likely impact to the target treatment population for the proposed chemotherapy treatment before making further investments.

Figure 6:
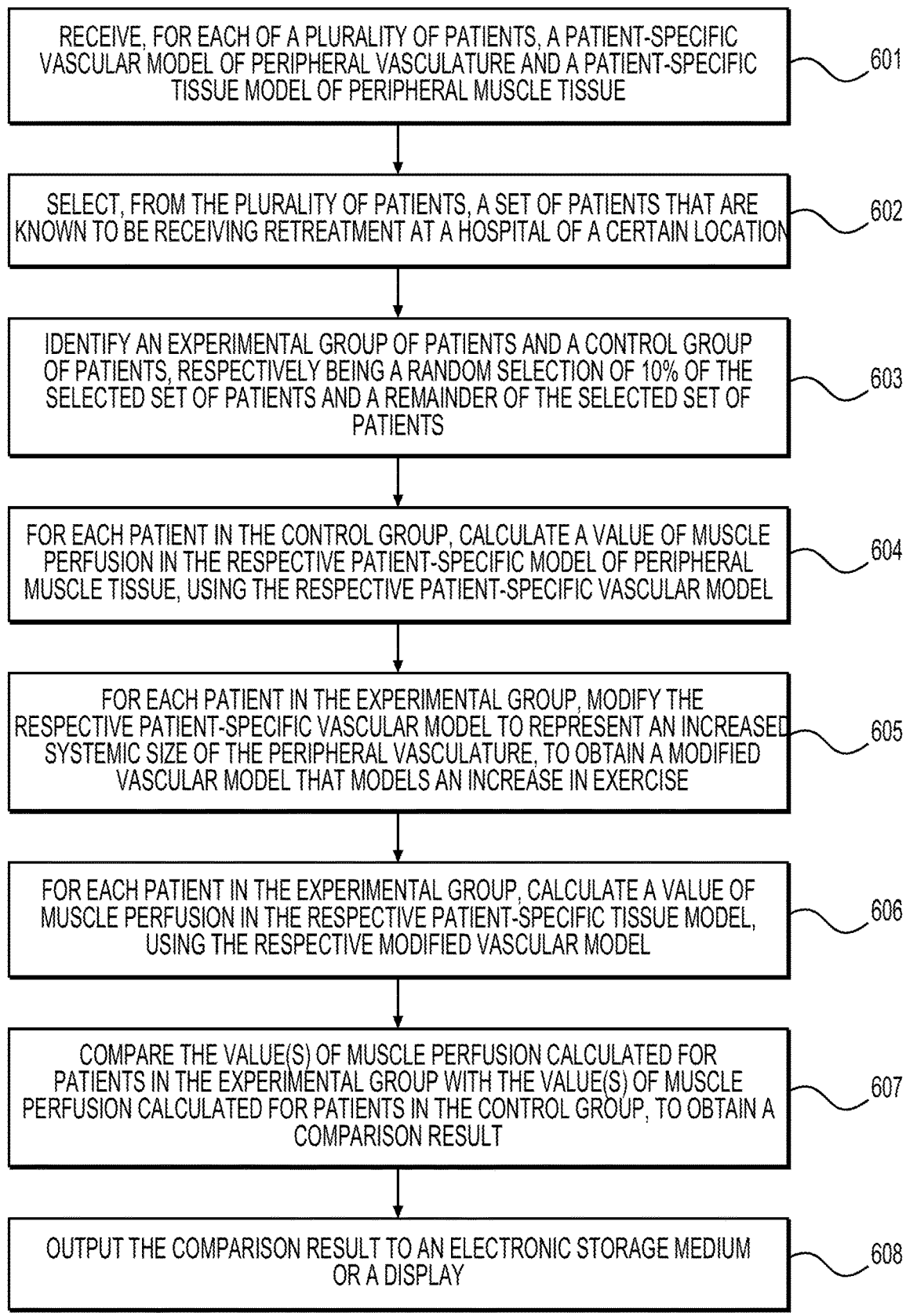
FIG. 6 depicts a flowchart of a method of performing computer-simulated evaluation of a land development project that may have a health impact, according to one or more embodiments.

FIG. 6 illustrates an example of a method for evaluating the health-related effects of a land development project, such as a new town park. As an example of a scenario in which the method may be utilized, a land use planner (e.g., an urban planner who is working for a city or town council) may desire to test the impact of a new or proposed town park on population health in order to assess its return on investment in health benefits in relation to the cost of building the park. Furthermore, the land use planner may desire to assess the impact of the town park on the prevalence of peripheral artery disease in the population.

The method illustrated by FIG. 6 may include steps 601-608, as will be discussed below. These steps may be understood as examples of steps 201-208 of the method illustrated by FIG. 2, respectively.

Step 601 may include receiving, for each of a plurality of patients, a patient-specific vascular model of peripheral vasculature and a patient-specific tissue model of peripheral muscle tissue. The model of peripheral vasculature may be an anatomical and/or physiological model. The model of peripheral muscle tissue may be an anatomical model. The models, along with patient-specific information for each of the plurality of patients, may be compiled in a database.

Step 602 may include selecting, from the plurality of patients, a set of patients that are receiving retreatment at a hospital of a certain location.

Step 603 may include identifying a control group of patients and an experimental group of patients. In the instant example, the experimental group may be a random selection of a certain percentage of the set selected in step 602, and the control group may be a remainder of the set selected in step 602. The percentage may represent the percentage of the patients expected to take advantage of the park. In the instant example, the percentage is 10%, but this percentage may be of a different value.

Step 604 may include, for each patient in the experimental group, calculating a value of muscle perfusion in the respective patient-specific tissue model, using the respective modified vascular model.

Step 605 may include, for each patient in the experimental group, modifying the respective patient-specific vascular model to represent an increased systemic size of the peripheral vasculature, to obtain a modified vascular model that models an increase in exercise. This increase in exercise is taken to be the effect of the new park on the patients.

Prior to step 605, the party or computer system performing the method may receive a description of the benefits that the new or proposed park may bring, and an evaluation endpoint. For example, the presence of a park may be expected to increase walking or other physical activity of patients, so as to result in health benefits for the patients. Such health benefits may be a reduction in diffuse intimal thickening of the peripheral vasculature of patients. A reduction in diffuse intimal thickening may be represented as, for example, a small percentage of systemic vasodilation in the peripheral vasculature. For purposes of representation in an anatomical or physiological model, this effect may be represented as an increase in the systemic size of the peripheral vasculature. In step 604, such increase may be modeled by adjustment of appropriate model parameters. The evaluation endpoint may be leg muscle perfusion under exercise (e.g., claudication).

Step 605 may include, for each patient in the experimental group, calculating a value of muscle perfusion in the respective patient-specific model of peripheral muscle tissue (without the modification to represent the increased system size), using the respective patient-specific tissue mode.

Step 607 may include comparing the value(s) of muscle perfusion calculated for patients in the experimental group with the value(s) of muscle perfusion calculated for patients in the control group, to obtain a comparison result. The method may further include outputting the comparison result to an electronic storage medium or a display (step 608).

The calculated muscle perfusion values or the comparison result may be used by the land use planner may assess the impact of building the new park on local population health (as assessed by claudication symptoms) when determining the return on the investment of building the new park.

It is noted that the methods illustrated in FIGS. 3-6 are not limited to the exact combination of features discussed above. In general, features in any particular one of the methods illustrated in FIGS. 3-6 may be combined with features of other methods, as well as features discussed earlier with reference to FIG. 2.

Further embodiments of the present disclosure relate to systems and methods for geomedicine. According to one or more embodiments of this disclosure, a method for geomedicine may include associating health-related characteristics with geography-related factors, and/or predicting health-related characteristics based on geography-related factors.

The process of associating health-related characteristics with geography-related factors may be performed be a computer system, and the results may be stored in a database. The process may include any one of the following: mapping physiologies, anatomies, or disease types of patients to one or more geography-related factors; mapping predictions of progression (e.g., of diseases or types of diseases) in patients or likely treatments that a patient may receive to geography-related factors with one or more geography-related factors; linking disease markers, such as disease markers of cardiovascular diseases with one or more geography-related factors; and linking characteristics of patients (e.g., a characteristic indicated by any of the aforementioned patient-specific information) to geography-related factors.

In general, any of the patient-specific information and evaluation endpoints discussed in relation to FIG. 2 may constitute health-related characteristics. Therefore, the process of associating health-related characteristics with geography-related factors may be performed using a database that includes, for each of a plurality of patients, one or more patient-specific models associated, and patient-specific information, as described in the above discussion for FIG. 2.

Examples of geography-related factors include geographical locations, geographically-related events, geographical features, environmental characteristics of geographical locations, and programs, development, and other investments made by a local city, district, or region. A geographical location may be a location of residence or employment of a person, or a location of a feature such as a hospital. Locations may be delineated at the county, state, or regional levels or at the level of various hospital catchment zones. Geography-related factors may also be proximity to one of the foregoing items, or a measure based on such proximity. For example, a geography-related factor may be proximity to a hospital.

Predicting health-related characteristics based on geography-related factors may include predicting the success or failure of local programs or investment in changing patient health characteristics, or predicting changes in health characteristics over a period of time due to effects of geography-related factors. The method of FIG. 6 serves as one example of predicting the effect of geography-related factors (e.g., a new park) on health-related characteristics (e.g., muscle perfusion). The methodology of FIG. 6 and FIG. 2 may be adapted to predict other types of health-related characteristics (as evaluation endpoints) based on geography-related factors. Accordingly, it becomes possible to develop a virtual therapy planner for a population or subpopulation, wherein the population or subpopulation may be represented by patients for which patient-specific models and patient-specific information exist.

Figure 7:
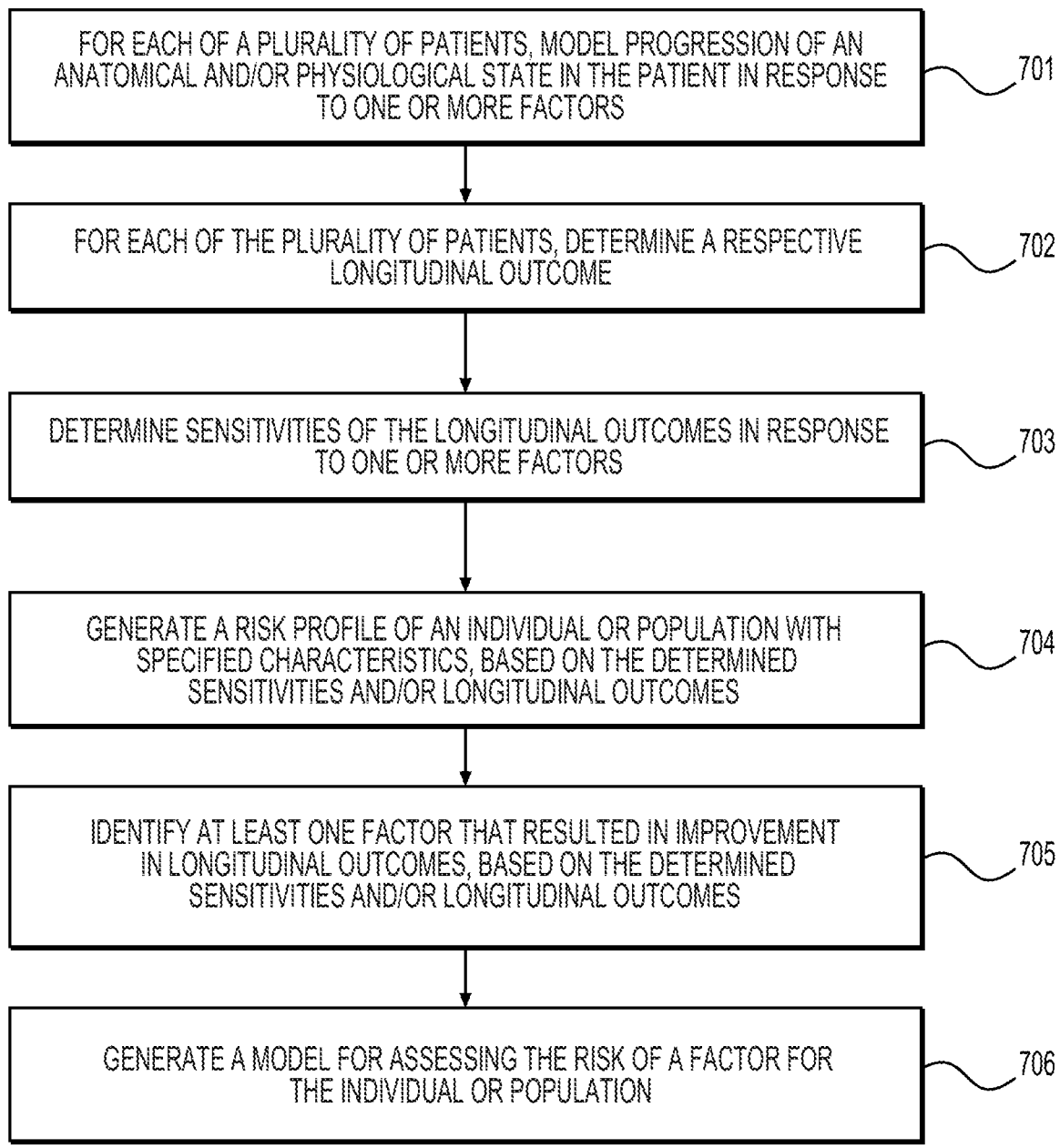
FIG. 7 illustrates a method for patient or subpopulation risk analysis.

Further embodiments of the present disclosure relate to systems and methods for patient or subpopulation risk analysis. FIG. 7 illustrates an example of a method for patient or subpopulation risk analysis. The method may utilize patient-specific data that includes, for each of a plurality of patients, one or more patient-specific models and patient-specific information associated with the respective patient. In general, the patient-specific data may have any of the features described in the above discussion for FIG. 2. The patient-specific data may be compiled and stored in a database of a computer system. The method of FIG. 7 may be performed by a computer system, such as sever systems 106 or a computer system of any suitable type.

Step 701 may include, for each of a plurality of patients, modeling progression of an anatomical and/or physiological state in the patient in response to one or more factors. The anatomical and/or physiological state may be, for example, a disease or other health-related condition of the patient. In some examples, the state may be the same disease across all of the plurality of patients.

The one or more factors may include one or more of the following: patient medical or health-related characteristic(s), patient behavioral characteristic(s), patient lifestyle characteristic(s), and patient environment characteristic(s), and treatment (e.g., any of the evaluation treatments discussed in this disclosure) received by the patient. Examples of medical or health-related characteristics include anatomical characteristics, physiological characteristics, genetic characteristics, pathological characteristics, co-morobidies, and characteristics indicated by clinical parameters.

In some examples, for each of the plurality of patients, the one or more factors include at least one physical, anatomical, and/or physiological characteristic of the patient (e.g., genetics and co-morobidies), and at least one of the following: environmental characteristic(s) of the patient, patient behavior or lifestyle, and a treatment received by the patient. In this context, physical characteristics may include gender, age, and ethnicity.

Different patients among the plurality of patients do not necessarily have to have the same factors or the same set of factors. However, in some examples, individual factors may be common to a subset of the plurality of patients, and other individual factors may be common to a different subset of the plurality of patients.

The modeling in step 701 may be based on patient-specific models. Patient-specific models may be of the types discussed for step 201 of FIG. 2, and may include, for example, anatomical and/or physiological models of vasculature and/or tissue. The modeling of the progression of an anatomical and/or physiological state may be performed by modifying a patient-specific model in a manner that models changes in anatomical and/or physiological characteristic(s) of a patient from one point in time to another point in time, wherein such changes may be dependent on the one or more factors. For example, the radii and thickness of arterial walls of patients may change over time due to natural aging and the progression of an anatomical and/or physiological state, and the manner of such change may depend on the one or more factors. In general, the techniques discussed above for step 205 of FIG. 2 for modifying a patient-specific model to model the effect of a treatment are also applicable to modifying a patient-specific model to model the effects of a passage of time under the presence of the one or more factors.

Step 702 may include, for each of the plurality of patients, determining a respective longitudinal outcome. The longitudinal outcomes may include one or more evaluation endpoints, which may be of the various types of evaluation endpoints discussed in this disclosure. Evaluation endpoints may be calculated using the techniques described above for step 206.

Step 703 may include determining sensitivities of the longitudinal outcomes in response to the one or more factors. The one or more factors may be each be among the factors considered in step 701. Step 703 may determine a relationship between the outcomes and the one or more factors, and such relationship may permit identification of certain factors (e.g., patient behavior, or usage of a product) that are correlated certain outcomes (e.g., outcomes that are better or more desirable).

Step 704 may include generating a risk profile of an individual or population with specified characteristic(s), based on the determined sensitivities and/or longitudinal outcomes. Such population may be a population in which the members of the population have the specified characteristic(s) in common, in which case the population may be referred to as a subpopulation. The risk profile may include a metric indicating risk (e.g., a risk score) for certain health-related conditions. For example, the risk profile may indicate that an individual or members of a population of certain specified characteristic(s) are more likely to have a disease or an evaluation endpoint of a certain value or range of values. In some examples, the specified characteristics include at least one physical, anatomical, and/or physiological characteristic.

Step 705 may include identifying at least one factor that resulted in improvement in longitudinal outcomes, based on the determined longitudinal outcomes and/or sensitivities. The at least one factor may be each be among the factors considered in step 701. In this context, "improvement" may be an improvement in longitudinal outcomes compared to cases in which the at least one factor was not present. Step 705 may be performed by identifying factors that correlate with favorable longitudinal outcomes, and finding those factors or combination of factors based on the correlation. In some examples, the at least one factor is a combination of: (a) at least one physical, anatomical, and/or physiological characteristic of the patient (e.g., genetics and co-morobidies); and (b) at least one of the following: environmental characteristic(s) of the patient, patient behavior or lifestyle, and a treatment received by the patient.

Step 706 may include generating a model for assessing the risk of a factor. In some examples, the factor is a factor that is among the one or more factors in step 703, or the at least one factor in step 705. The factor may be, for example, an environmental characteristic, a behavior, a lifestyle, or a treatment. The model may be a financial model for pricing the risk of the factor. The model may be at a population level and/or at an individual level, and may apply to the individual or the population in step 704. The models may be generated based on the risk profile.

According to the method of FIG. 7, it becomes possible for individuals to understand the impact of choices related to health and treatments and the range and probabilities of outcomes given their choices. It also becomes possible for entities, such as marketers, actuaries, and public services, to understand the financial impact and outcomes of products, services on populations and individuals. As described above, any process discussed in this disclosure that is understood to be computer-implementable may be performed by one or more processors of a computer system. A processor may be a central processing unit (CPU), a graphics processing unit (GPU), or another type of processing unit. The one or more processors may be configured to perform such processes by having access to instructions (e.g., software or computer-readable code) that, when executed by the one or more processors, cause the one or more processors to perform the processes. As mentioned, such instructions may be stored in a memory of the computer system. Alternatively or additionally, such instructions may be stored on a non-transitory computer-readable medium.

Therefore, whenever a computer-implemented method is described in this disclosure, this disclosure shall also be understood as describing a non-transitory computer-readable medium storing instructions that, when executed by one or more processors, cause the one or more processors to perform the computer-implemented method. Examples of non-transitory computer-readable medium include RAM, ROM, solid-state storage media (e.g., solid state drives), optical storage media (e.g., optical discs), and magnetic storage media (e.g., hard disk drives). A non-transitory computer-readable medium may be part of the memory of a computer system or separate from any computer system.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted.

What is claimed is:

1. A computer-implemented method for performing computer-simulated evaluation of treatments, the method comprising:

for each of a plurality of patients, receiving one or more patient-specific anatomical and/or physiological models, the one or more patient-specific models including a model of at least a portion of a vasculature of the respective patient;

selecting, from the plurality of patients, a set of patients that have one or more common characteristics;

identifying an experimental group of patients from the set of patients;

for each patient in the experimental group, modifying at least one model of the respective one or more patient-specific models to obtain at least one modified patient-specific model that models an effect of an evaluation treatment on the respective patient, and calculating a value of an evaluation endpoint based on the respective at least one modified patient-specific model, the evaluation endpoint being indicative of a health or medical characteristic of a patient; and comparing the calculated values of the evaluation endpoint with one or more control values of the evaluation endpoint for patients that satisfy the one or more selection criterion.

2. The method of claim 1, further comprising identifying a control group of patients from the set of patients; and calculating the control values of the evaluation endpoint by, for each patient in the control group of patients, calculating a control value of the evaluation endpoint based on the one or more patient-specific models received for the respective patient.

3. The method of claim 1, wherein the evaluation treatment is one or more of: a revascularization, a surgery, a medication, weight gain or loss, organ transplantation, recanalization, a social policy change, a diet change, smoking cessation, a relocation, an environmental change, a genetic change, plaque regression or progression, immunotherapy, and use of a medical device or implant.

4. The method of claim 1, wherein the evaluation endpoint is one or more of:

a fractional flow reserve (FFR);

an instantaneous wave-free ratio (iFR);

a coronary flow reserve (CFR);

a synergy between PCI with Taxus and Cardiac Surgery (SYNTAX) score;

a risk of major adverse cardiac events (MACE);

a percent stenosis;

an indicia, value, or characteristic of perfusion;

an indicia, value, or characteristic of plaque regression and/or progression; an indicia, value, or characteristic of plaque rupture; and an indicia, value, or characteristic of thrombosis; and an indicia, value, or characteristic of organ function.

5. The method of claim 1, wherein for each of the plurality of patients, the one or more patient-specific models further includes a patient-specific tissue model of a tissue of the respective patient.

6. The method of claim 5, wherein the vasculature is a coronary vasculature, the tissue is a myocardial heart tissue, and for each patient in the experimental group, the at least one modified patient-specific model is a modified vascular model obtained by modification of the respective model of the at least the portion of the vasculature.

7. The method of claim 6, wherein the one or more common characteristics includes having coronary artery disease, the effect of the evaluation treatment is an opening of vascular sections with soft plaque, and the evaluation endpoint is a value of fractional flow reserve (FFR) of at least a vessel portion of a vascular model.

8. The method of claim 7, wherein
the one or more common characteristics includes an age characteristic,
the effect of the evaluation treatment is an increase of adipose tissue, and
the evaluation endpoint is rupture risk.

9. The method of claim 5, wherein the evaluation endpoint is an indicia, value, or characteristic of perfusion in the tissue.

10. The method of claim 9, wherein
the vasculature is a peripheral vasculature,
the tissue is a peripheral muscle tissue, and
the effect of the evaluation treatment is an increase in a systemic size of the peripheral vasculature.

11. The method of claim 1, wherein
for each of the plurality of patients, the model of the at least the portion of the vasculature is a heart model,
the one or more common characteristics includes having a myocardial infarction,
the effect of the evaluation treatment is a usage of a pacemaker, and
the evaluation endpoint is an ejection fraction calculated using the heart model.

12. A computer system for performing computer-simulated evaluation of treatments, comprising:
a memory storing instructions;
one or more processors configured to execute the instructions to perform operations including:
for each of a plurality of patients, receiving one or more patient-specific anatomical and/or physiological models, the one or more patient-specific models including a model of at least a portion of a vasculature of the respective patient;
selecting, from the plurality of patients, a set of patients that have one or more common characteristics;
identifying an experimental group of patients from the set of patients;
for each patient in the experimental group,
modifying at least one model of the respective one or more patient-specific models to obtain at least one modified patient-specific model that models an effect of an evaluation treatment on the respective patient, and
calculating a value of an evaluation endpoint based on the respective at least one modified patient-specific model, the evaluation endpoint being indicative of a health or medical characteristic of a patient; and
comparing the calculated values of the evaluation endpoint with one or more control values of the evaluation endpoint for patients that satisfy the one or more selection criterion.

13. The computer system of claim 12, wherein the operations further comprise:
identifying a control group of patients from the set of patients; and
calculating the control values of the evaluation endpoint by, for each patient in the control group of patients, calculating a control value of the evaluation endpoint based on the one or more patient-specific models received for the respective patient.

14. The computer system of claim 12, wherein for each of the plurality of patients, the one or more patient-specific models includes a patient-specific tissue model of a tissue of the respective patient.

15. The computer system of claim 14, wherein
the vasculature is a coronary vasculature, and
the tissue is a myocardial heart tissue, and
for each patient in the experimental group, the at least one modified patient-specific model is a modified vascular model obtained by modification of the respective model of the at least the portion of the vasculature.

16. The computer system of claim 15, wherein
the one or more common characteristics includes having coronary artery disease,
the effect of the evaluation treatment is an opening of vascular sections with soft plaque, and
the evaluation endpoint is a value of fractional flow reserve (FFR) of at least a vessel portion of a vascular model.

17. The computer system of claim 16, wherein
the one or more common characteristics includes an age characteristic,
the effect of the evaluation treatment is an increase of adipose tissue, and
the evaluation endpoint is rupture risk.

18. The computer system of claim 14, wherein the evaluation endpoint is an indicia, value, or characteristic of perfusion in the tissue.

19. The computer system of claim 12, wherein
for each of the plurality of patients, the model of the at least the portion of the vasculature is a heart model,
the one or more common characteristics includes having a myocardial infarction,
the effect of the evaluation treatment is a usage of a pacemaker, and
the evaluation endpoint is an ejection fraction calculated using the heart model.

20. A non-transitory computer-readable medium storing instructions that, when executed by one or more processors of a computer system, cause the one or more processors to perform a method for performing computer-simulated evaluation of treatments, the method comprising:
for each of a plurality of patients, receiving one or more patient-specific anatomical and/or physiological models, the one or more patient-specific models including a model of at least a portion of a vasculature of the respective patient;
selecting, from the plurality of patients, a set of patients that have one or more common characteristics;
identifying an experimental group of patients from the set of patients;
for each patient in the experimental group,
modifying at least one model of the respective one or more patient-specific models to obtain at least one modified patient-specific model that models an effect of an evaluation treatment on the respective patient, and
calculating a value of an evaluation endpoint based on the respective at least one modified patient-specific model, the evaluation endpoint being indicative of a health or medical characteristic of a patient; and
comparing the calculated values of the evaluation endpoint with one or more control values of the evaluation endpoint for patients that satisfy the one or more selection criterion.

* * * * *

UNITED STATES PATENT AND TRADEMARK OFFICE
CERTIFICATE OF CORRECTION

PATENT NO. : 10,991,465 B2
APPLICATION NO. : 16/226204
DATED : April 27, 2021
INVENTOR(S) : Leo Grady Page 1 of 1

It is certified that error appears in the above-identified patent and that said Letters Patent is hereby corrected as shown below:

In the Claims

Column 21, Line 5, in Claim 8, delete "adispose" and insert --adipose--.
Column 22, Line 21, in Claim 17, delete "adispose" and insert --adipose--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*